United States Patent [19]
Morris et al.

[11] Patent Number: 5,514,122
[45] Date of Patent: May 7, 1996

[54] FEMININE HYGIENE PAD

[75] Inventors: Terry L. Morris, Eagan; Ying-Yuh Lu, Woodbury; Michele M. Parker, St. Paul; Joaquin Delgado, Stillwater, all of Minn.

[73] Assignee: Minnesota Mining and Manufacturing Company, St. Paul, Minn.

[21] Appl. No.: 243,469

[22] Filed: May 16, 1994

[51] Int. Cl.⁶ .............................. A61F 13/56; A61L 15/58
[52] U.S. Cl. .................. 604/387; 428/343; 428/355; 604/389
[58] Field of Search .................. 428/343, 355; 604/387, 389

[56] References Cited

U.S. PATENT DOCUMENTS

| | | | |
|---|---|---|---|
| 3,620,988 | 11/1971 | Cohen | 260/17.4 |
| 3,922,464 | 11/1975 | Silver et al. | 428/355 |
| 3,925,442 | 12/1975 | Samour | 260/459 |
| 3,983,166 | 9/1976 | Samour | 260/481 R |
| 4,166,152 | 8/1979 | Baker et al. | 428/522 |
| 4,337,772 | 7/1982 | Roeder | 128/290 R |
| 4,379,201 | 4/1983 | Heilmann et al. | 428/345 |
| 4,495,318 | 1/1985 | Howard | 524/375 |
| 4,598,112 | 7/1986 | Howard | 524/78 |
| 4,629,663 | 12/1986 | Brown et al. | 428/343 |
| 4,645,783 | 2/1987 | Kinoshita | 523/221 |
| 4,735,837 | 4/1988 | Miyasaka et al. | 428/40 |
| 4,786,696 | 11/1988 | Bohnel | 526/88 |
| 4,810,763 | 3/1989 | Mallya et al. | 526/203 |
| 5,045,569 | 9/1991 | Delgado | 521/60 |
| 5,053,436 | 10/1991 | Delgado | 521/64 |
| 5,118,750 | 6/1992 | Silver et al. | 524/462 |
| 5,201,727 | 4/1993 | Nakanishi | 604/390 |

FOREIGN PATENT DOCUMENTS

| | | | |
|---|---|---|---|
| 0401509 | 12/1990 | European Pat. Off. | C09J 7/02 |
| 0439941 | 8/1991 | European Pat. Off. | C09J 7/02 |
| 0554832 | 8/1993 | European Pat. Off. | C09J 7/02 |
| 3544882 | 11/1986 | Germany | C08L 33/06 |
| WO89/12618 | 12/1989 | WIPO | C07C 41/16 |
| WO91/11334 | 7/1992 | WIPO | C09J 133/08 |

OTHER PUBLICATIONS

*Die Angewandte Makromolekulare Chemie*, 132 (1985), Synthesis and Polymerization of a Styryl Terminated Oligovinylpyrrolidone Macromonomer, pp. 81–89.

*Journal of Applied Polymer Science*, vol. 39, 2027–2030 (1990), Notes, Graft Copolymers Having Hydrophobic Backbone and Hydrophilic Branches. V.

*Journal of Polymer Science: Part A: Polymer Chemistry*, vol. 27, 3521–3530 (1989), Graft Copolymers Having Hydrophobic Backbone and Hydrophilic Branches. IV.

*Primary Examiner*—Jenna L. Davis
*Attorney, Agent, or Firm*—Gary L. Griswold; Walter N. Kirn; William J. Bond

[57] ABSTRACT

A feminine hygiene pad is provided with a linerless microsphere pressure-sensitive adhesive attachment region for attaching the pad to an undergarment. The pads are stackable without release liners and can be used as a tape to form the liquid barrier backing of the pad.

31 Claims, 1 Drawing Sheet

5,514,122

FEMININE HYGIENE PAD

BACKGROUND AND FIELD OF THE INVENTION

This invention relates to a simplified attachment system for a feminine hygiene pad or adult absorbent napkin, or the like.

Feminine sanitary napkins and adult incontinent pads come in a wide variety of shapes and sizes, however, all generally employ a liquid impermeable barrier sheet coated or supplied with an adhesive attachment region(s). This adhesive is invariably protected by a release liner prior to attachment of the sanitary napkin or incontinent pad to the fabric undergarment of the user. This adhesive attachment region is conventionally a hot-melt coated adhesive which is coated onto a release liner immediately prior to application of the adhesive coated liner to the liquid impermeable barrier sheet. This adhesive then transfers from the release liner onto the barrier sheet. The release liner is left in place to protect the adhesive from contamination or from transfer to adjacent incontinent pads or sanitary napkins or packaging materials in the package prior to use. The hot-melt coated adhesive is generally a synthetic rubber-resin type adhesive.

An alternative method would be to use a release liner having differential release coatings on both faces, which is then formed into a roll of tape. This tape could then be unwound on the production line and applied to the sanitary napkin or incontinent pad. Although this method avoids many of the problems in hot-melt coating directly on the, e.g., sanitary napkin production line, it adds to material cost.

Recently, there has been significant interest in eliminating the detachable release liner on sanitary napkins and adult incontinent pads. A considerable number of recent patents have addessed this issue. However the approaches generally proposed have also relied on use of synthetic rubber-resin type adhesives and the release liner is made an integral portion of the sanitary napkin or incontinent pad such that it would not require separate disposal. The release liner is therefore not eliminated rather made so that it does not require separate disposal. These designs demand quite complicated manufacturing techniques requiring the use of elaborate tape laminate structures, where a preformed tape is employed, or the need for elaborate tape forming and coating techniques for on-line production. The sanitary napkin, or the like, must also be precisely folded onto itself to bring the release liner into registered contact with the adhesive, adding further complications to the manufacturing process.

SUMMARY OF THE INVENTION

The present invention seeks to eliminate the need for release liners on conventional sanitary napkins or adult incontinent pads, or the like, by using an acrylic or acrylate pressure-sensitive adhesive(PSA) matrix or binder containing at least 1 percent and up to 60 percent inherently elastic, tacky, solvent and water insoluble, crosslinked solvent dispersible polymeric microspheres formed by free radically polymerizable monomers where the polymer or copolymer has a glass transition temperature of generally less than $-10°$ C. The tacky microspheres in an acrylate PSA binder or matrix can be coated onto a barrier backing, preferably a thin polyethylene film. This adhesive coated barrier backing can then be wound for later use into a roll of tape or used to directly produce a feminine hygiene sanitary napkin or adult incontinent pad, where the barrier backing forms the liquid impermeable backsheet and with no need for separate application of a release liner. Alternatively, the microspheres in an acrylate PSA matrix can be coated onto a barrier backing during the production process of the sanitary napkin or adult incontinent pad, and subsequently packaged without any need for a separately disposable release liner. The microsphere/acrylate adhesive provides secure attachment to a conventional fabric such as cotton, however, does not transfer onto adjacent sanitary napkins or adult incontinent pads, or packaging film when in the package prior to use. Also, when supplied in a tape form with the barrier backing, the barrier backing need not be release coated to facilitate tape unwind, which could interfere with subsequent manufacture of the absorbent pad or sanitary napkin.

DETAILED DESCRIPTION OF THE INVENTION

Figure 1:
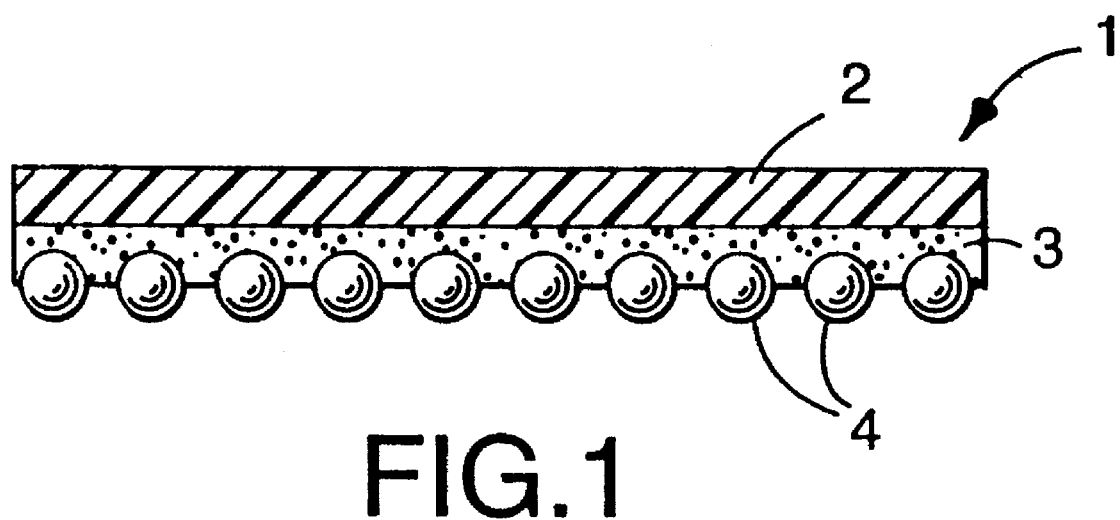
FIG. 1 is a side perspective view of an expanded idealized microsphere film formed according to the invention.

The inherently elastic or tacky, solvent and water insoluble such that a portion of the polymer is water and solvent insoluble, crosslinked, solvent or water dispersible, polymeric microspheres are formed primarily from free radically polymerizable monomers preferably capable of forming homo- or co-polymers having glass transition temperatures or melt transition temperatures generally less than $-10°$ C. Preferred are vinyl esters, acrylates and methacrylates which will produce homopolymers or copolymers having glass transition temperatures less than $0°$ C., preferably less than $-10°$ C. Suitable acrylates and methacrylates include isooctyl acrylate, isononyl acrylate, isoamyl acrylate, 2-ethylhexyl acrylate, n-butyl acrylate, and sec-butyl acrylate; other acrylates and methacrylates can be used provided that the overall Tg is less than that specified, such other monomers include terbutyl acrylate, isobornyl acrylate, butyl methacrylate, vinyl acetate, acrylonitrile, isononal acrylate, isodecyl acrylate, isodecyl methacrylate, sec-butyl acrylate, isoamyl acrylate, 2-methylbutyl acrylate, 4-methyl-2-pentyl acrylate, isodecyl acrylate, and ethyl acrylate; mixtures thereof with vinyl esters and other suitable comonomers.

Vinyl ester monomers suitable for use in this invention include but are not limited to those selected from the group consisting of vinyl 2-ethylhexanoate, vinyl caprate, vinyl laurate, vinyl pelargonate, vinyl hexanoate, vinyl propionate, vinyl decanoate, vinyl octanoate, and other monofunctional unsaturated vinyl esters of linear or branched carboxylic acids comprising 1 to 14 carbon atoms which as homopolymers have glass transition temperatures below about $-10°$ C. Preferred vinyl ester monomers include those selected from the group consisting of vinyl laurate, vinyl caprate, vinyl-2-ethylhexanoate, and mixtures thereof.

Styrene and substituted styrenes are suitable monomers used in conjunction with the vinyl esters, acrylates or methacrylates. Also useful as comonomers are other vinyl monomers such as vinyl benzene, N-i-octylacrylamide, vinyl chloride and vinylidene chloride, which monomers can be used in conjunction with the vinyl ester, acrylate, methacrylate or acrylic monomers. Minor amounts of other comonomers known in the art can be employed, provided that the Tg of the resulting copolymer stays within the desired range.

The polar monomers useful in the present invention are both somewhat oil-soluble and water soluble, resulting in a distribution of the polar monomer between the aqueous or polar phase and the oil phase. Representative examples of suitable polar monomers include, but are not limited to, those selected from the group consisting of acrylic acid, methacrylic acid, itaconic acid, crotonic acid, maleic acid, fumaric acid, sulfoethyl methacrylate, and ionic monomers such as sodium methacrylate, ammonium acrylate, sodium acrylate, trimethylamine p-vinyl benzimide, 4,4,9-trimethyl-4-azonia-7-oxo-8-oxa-dec-9-ene-1-sulphonate, N,N-dimethyl-N-(beta-methacryloxy-ethyl) ammonium propionate betaine, trimethylamine methacrylimide, 1,1-dimethyl-1-(2, 3-dihydroxypropyl)amine methacrylimide, N-vinyl pyrrolidone, N-vinyl caprolactam, acrylamide, t-butyl acrylamide, dimethyl amino ethyl acrylamide, N-octyl acrylamide, mixtures thereof, and the like. Preferred polar monomers include those selected from the group consisting of monoolefinic monocarboxylic acids, monoolefinic dicarboxylic acids, acrylamides, N-substituted acrylamides, salts thereof, and mixtures thereof. Examples of such monomers include but are not limited to those selected from the group consisting of acrylic acid, sodium acrylate, N-vinyl pyrrolidone, and mixtures thereof.

Hydrophilizing agents or components can also be used with the monomers and produce microspheres with pendent hydrophilic moieties. The hydrophilizing agents can act as crosslinkers when they are multi-funcional. Preferred are free radically reactive hydrophilic oligomers(a polymer having a low number of repeating units, generally 2 to 20) and/or polymers(having more repeating units than an oligomer) including but are not limited to those selected from the group consisting of poly(alkylene oxides), such as poly(ethylene oxide), poly(vinyl methyl ether), poly(acrylamide), poly(n-vinylpyrrolidone), poly(vinyl alcohol), cellulose derivatives and mixtures thereof.

Preferred macromonomers include those selected from the group consisting of acrylate terminated poly(ethylene oxide), methacrylate terminated poly(ethylene oxide), methoxy poly(ethylene oxide) methacrylate, butoxy poly(ethylene oxide) methacrylate, p-vinyl benzyl terminated poly(ethylene oxide), acrylate terminated poly(ethylene glycol), methacrylate terminated poly(ethylene glycol), methoxy poly(ethylene glycol) methacrylate, butoxy poly(ethylene glycol) methacrylate, p-vinyl benzyl terminated poly(ethylene glycol), poly(ethylene oxide) diacrylate, poly(ethylene oxide) dimethacrylate, and mixture thereof. These functionalized materials are preferred because they are easily prepared through well-known ionic polymerization techniques and are also highly effective in providing grafted hydrophilic segments along free radically polymerized microsphere polymer backbones.

Preferred macromonomers also include those selected from the group consisting of p-vinyl benzyl terminated poly(n-vinyl pyrrolidone), p-vinyl benzyl terminated poly-(acrylamide), methacrylate terminated poly(n-vinyl pyrrolidone), p-vinyl benzyl terminated poly(acrylamide), and mixtures thereof. These macromonomers may be prepared through the esterification reaction of a carboxy terminated n-vinyl pyrrolidone or acrylamide, beta-mercaptopropionic acid chain transfer agent, and chloromethyl styrene or methacryloyl chloride as described in a series of papers by M. Acacia et al. [*Angew. Makromol. Chem.*, 132, 81 (1985); *J. Appl. Polym. Sci.*, 39, 2027 (1990); *J. Polym. Sci.*, Part A: *Polym. Chem.*, 27, 3521 (1989)], all incorporated by reference herein.

The microspheres of this invention preferably comprise at least about 70 parts of at least one free radically polymerizable monomer, optionally up to about 30 parts of one or more polar monomers, and about 0 to about 30 parts of at least one hydrophilizing component. Additional initiators and/or multifunctional crosslinker and other additives may also be used in addition to the above.

More preferably, the microspheres comprise about 80 to about 100 parts, most preferably 90 to 100 parts, of free radically polymerizable monomer selected from the group consisting of alkyl acrylate esters, alkyl methacrylate esters, vinyl esters, and mixtures thereof where the alkyl group is a $C_4$ to $C_{12}$ alkyl, optionally about 0 to about 10 parts of at least one polar monomer, and optionally about 0 to about 10 parts of a hydrophilizing component. Most preferably the microspheres comprise about 95 to about 99.9 parts of free radically polymerizable monomer, about 0 to about 5.0 parts of a hydrophilizing component, and, optionally, about 0.1 to about 5.0 parts of a polar monomer.

Aqueous suspensions of hollow microspheres of the invention may be prepared by known "two-step" emulsification processes where the first step involves forming a water-in-oil emulsion of an aqueous solution with an oil phase of the free radically polymerizable monomer formed with an emulsifier having a low hydrophilic-lipophilic balance (HLB) value (i.e., less than 7.0), preferably 2 to 7.

Also included in the oil phase would by any free radical initiator, optional comonomers, the polar monomer, crosslinking monomers or oligomers, or conventional additives.

In the second step, a water-in-oil-in-water emulsion is formed by dispersing the water-in-oil emulsion from the first step into an aqueous phase containing an emulsifier having a HLB value of above 6. In both steps, when an emulsifier is utilized, its concentration should be greater than its critical micelle concentration, which is defined as the minimum concentration of emulsifier necessary for the formation of micelles, i.e., submicroscopic aggregations of emulsifier molecules. Critical micelle concentration is slightly different for each emulsifier, suitable concentrations ranging from about $1.0 \times 10^{-4}$ to about 3.0 moles/liter.

The hydrophilizing component can be added to the oil or water phase in the first step or the water phase in the second step, either before or after polymerization is initiated, or some combination of these options.

Hollow microspheres which may contain polar monomer(s) may also be prepared by a "one-step" emulsification process comprising the aqueous suspension polymerization of the free radically polymerizable monomer(s), at least one hydrophilizing component, and, optionally, at least one polar monomer in the presence of at least one emulsifier capable of producing a water-in-oil emulsion or droplets inside the liquid phase, which droplets are substantially stable during emulsification and the subsequent polymerization. As in the two-step emulsification process, the emulsifier is utilized in concentrations greater than its critical micelle concentration.

Solid microspheres may be prepared by a "one-step" emulsification process comprising an aqueous suspension polymerization of the free radically polymerizable monomer(s), at least one hydrophilizing component, an emulsifier or suspension stabilizers, optionally at least one polar monomer, oil soluble initiator(s), optionally crosslinkers, and other optional additives in an aqueous or other polar solution. Methods for suspension polymerization include these described in patents such as U.S. Pat. Nos. 3,620,988; 4,166,152; 4,495,318; 4,598,112; 4,810,763; DE 3,544,882;

4,786,696 or 4,645,783. The suspension can be stabilized by polymeric stabilizers, include those described in U.S. Pat. No. 4,166,152 (Baker et al., including but not limited to casein, crosslinked polyacrylic acids, polyoxyethylene, polyacrylic acid, polymethacrylic acid, polyacrylamide, polyvinyl pyrrolidone, polyethylene amine, polyvinyl methyl ether, polyvinyl alcohol, salts thereof, and mixtures thereof). Polymeric stabilizers or mechanical agitation can be used alone or in conjunction with ionic or nonionic surfactants or emulsifiers. Preferred are suspension polymerization processes using ionic or nonionic emulsifiers at a concentration greater than the critical micelle concentration.

In all of the above methods, all or part of the hydrophilizing component(s), and the polar monomer(s) can be added after the free radical monomer polymerization of the oil emulsion is initiated. This may be done provided that the withheld components are added to the polymerizing mixture prior to 100% conversion of the monomers to polymer.

Suitable initiators are those which are normally suitable for free radical polymerization of free radically polymerizable monomers and which are oil-soluble and of very low solubility in water. Examples of such initiators include but are not limited to those selected from the group consisting of thermally-activated initiators such as azo compounds, hydroperoxides, peroxides, and the like, and photoinitiators such as benzophenone, benzoin ethyl ether, and 2,2-dimethoxy-2-phenyl acetophenone, and the like, and mixtures thereof. Use of a water soluble polymerization initiator causes formation of substantial amounts of latex which is generally undesirable. The initiator is generally used in an amount ranging from about 0.01 percent up to about 10 percent by weight of the total polymerizable composition (i.e., monomers, hydrophilizing component, and initiator), preferably up to about 5 percent.

The composition from which the microspheres of the invention are made may also contain a multifunctional crosslinking agent to render at least a portion of the microspheres solvent and water insoluble. The term "multifunctional" as used herein refers to crosslinking agents which possess two or more free radically polymerizable ethylenically unsaturated groups. Useful multifunctional crosslinking agents include those selected from the group consisting of acrylic or methacrylic esters of diols such as butanediol diacrylate, triols such as glycerol, and tetraols such as pentaerythritol. Other useful crosslinking agents include those selected from the group consisting of polymeric multifunctional (meth)acrylates, e.g., poly(ethylene oxide) diacrylate or poly(ethylene) oxide dimethacrylate; polyvinylic crosslinking agents, such as substituted and unsubstituted divinylbenzene; and difunctional urethane acrylates, such as "EBECRYL" 270 and "EBECRYL" 230 (1500 weight average molecular weight and 5000 weight average molecular weight acrylated urethanes, respectively—both available from Radcure Specialties), and mixtures thereof. The amount of crosslinker used will depend on the equivalent weight of the crosslinker and the monomer (equivalent weight=molecular weight divided by polymerizable functional groups per molecule). Generally, the amount of the crosslinking functional groups comprises up to about 0.15% of the total polymerizable functional groups. The crosslinker can be added to any phase at any time before 100% conversion to polymer of the monomers of this microsphere composition. Preferably, crosslinker is added before initiation occurs.

The microspheres of the invention are normally elastomeric, tacky, solvent and water insoluble but swellable in organic solvents, and small, typically having diameters of at least about 1 micron, preferably in the range of about 1 to about 300 microns, and most preferable about 1 to 150 microns, or most preferably 20 to 150 microns. When the microspheres are hollow, the voids typically range in size from less than 1 micron up to about 100 microns or larger.

Following polymerization by any of these one-step or two-step processes, an aqueous suspension of the hollow or solid microspheres is obtained which is stable to agglomeration or coagulation under room temperature conditions (i.e., about 20° to about 25° C.). The suspension may have a non-volatile solids content of from about 10 to about 60 percent by weight. Upon prolonged standing, the suspension can separate into two phases, one phase being aqueous and substantially free of polymer, the other phase being an aqueous suspension of microspheres. Both phases may contain a minor portion of submicron latex particles.

Decantation of the microsphere-rich phase provides an aqueous suspension having a non-volatile solids content on the order of about 40 to about 65 percent which, if shaken with water, will readily redisperse. The suspension may be coated on suitable flexible or inflexible backing materials with an adhesive binder by conventional coating techniques such as knife coating or Meyer bar coating or use of an extrusion die.

Once dried, the microspheres, with sufficient agitation, will readily disperse in common organic liquids such as ethyl acetate, tetrahydrofuran, heptane, 2-butanone, benzene, cyclohexane, and esters. Solvent dispersions of the microspheres may also be coated with an adhesive binder on at least one side of a suitable backing material by conventional coating techniques, as described above for aqueous suspensions.

The pressure-sensitive adhesive properties of the microspheres may be altered by the addition of tackifying resin and/or plasticizer. It is also within the scope of this invention to include various other components, such as pigments, neutralizing agents such as sodium hydroxide, etc., fillers, stabilizers, chain transfer agents or various polymeric additives.

The pressure-sensitive adhesive matrix or binder is preferably a free radically polymerizable acrylate pressure-sensitive adhesive composition which is preferably prepared by an emulsion polymerization process. These acrylates are typically alkyl acrylates, preferably monofunctional unsaturated acrylate esters of non-tertiary alkyl alcohols, the alkyl groups of which have from 2 to about 14 carbon atoms providing a polymer having a Tg of less than 0° C., preferably less than −10° C. Included with this class of monomers are, for example, isooctyl acrylate, isononyl acrylate, 2-ethyl-hexyl acrylate, decyl acrylate, dodecyl acrylate, n-butyl acrylate, and hexyl acrylate.

Preferred monomers include isooctyl acrylate, isononyl acrylate, 2-ethylhexyl acrylate, butyl acrylate or mixtures thereof. The alkyl acrylate monomers can be used to form homopolymers or they can be copolymerized with polar copolymerizable monomers or higher Tg monomers (higher than the alkyl acrylate) such as vinyl esters, $C_1$ to $C_{14}$ alkyl esters of (meth)acrylic acid and/or styrene. When copolymerized with strongly polar monomers, the alkyl acrylate monomer generally comprises at least about 75% of the polymerizable monomer composition. When copolymerized with moderately polar monomers, the alkyl acrylate monomer generally comprises at least about 70% of the polymerizable monomer composition. High Tg monomers can be used in amounts up to 20% of the monomer composition, preferably from 3 to 15 percent, most preferably 6 to 10 percent.

The polar copolymerizable monomers can be selected from strongly polar monomers such as monoolefinic mono- and dicarboxylic acids, hydroxyalkyl acrylates, cyanoalkyl acrylates, acrylamides or substituted acrylamides, or from moderately polar monomers such as N-vinyl pyrrolidone, acrylonitrile, vinyl chloride or diallyl phthalate. The strongly polar monomer preferably comprises up to about 25%, more preferably up to about 15%, of the polymerizable monomer composition. The moderately polar monomer preferably comprises up to about 30%, more preferably from about 2% to about 20% of the polymerizable monomer composition.

Optionally a low molecular weight hydrophobic polymer can be added to the adhesive matrix monomers to improve emulsion stability. These polymers would have an average molecular weight of from 400 to 50,000 and include polystyrene resins, poly(methylmethacrylate) resin, polybutadiene, polyisoprene, poly(alphamethylstyrene), polydiene-polyaromatic arene copolymers, rosin esters and mixtures thereof. These could be added in amounts up to 20 percent of the monomer mixture, preferably 0–10 percent.

Also usable are copolymerizable ionic surfactants to improve cohesive strength and moisture resistance. These include polyalkylene polyalkoxy ammonium sulfate (e.g., "MAZON" SAM-211 available from PPG Industries) and alkyl allyl sulfosuccinates (e.g., "TREM" LF40 available from Diamond Shamrock Co.) as well as those described in PCT application No. WO 89/12618, U.S. Pat. Nos. 3,925,442 and 3,983,166, incorporated herein by reference. Other noncopolymerizable ionic and nonionic surfactants can be used above or in blends instead of the copolymerizable surfactants but are less preferred. The surfactants can be used in amounts of from 0 to 10 percent of the total monomer component, preferably 1.5 to 5 percent.

The pressure-sensitive adhesive matrix of the invention also contains initiator to aid in polymerization of the monomers. Suitable initiators include thermally-activated initiators where the initiator can be water or oil soluble. Suitable oil soluble initiators include azo, and diazo compounds, hydroperoxides, peroxides, and the like. Water soluble initiators include persulfates such as potassium persulfate. Generally, the initiator is present in an amount of from about 0.01 percent to about 3.0 percent, preferably 0.1 to 0.5 percent, based on the total monomer component.

Where superior cohesive strengths are desired, the pressure-sensitive adhesive matrix may also be cross-linked. Preferred crosslinking agents for the acrylic pressure-sensitive adhesive matrix are multiacrylates such as 1,6-hexanediol diacrylate as well as those disclosed in U.S. Pat. No. 4,379,201 (Heilmann et al.), incorporated herein by reference. Photo-initiators can act as post-cure crosslinkers, such as the benzoin ethers, substituted benzoin ethers such as benzoin methyl ether or benzoin isopropyl ether, substituted acetophenones such as 2,2-diethoxyacetophenone, and 2,2-dimethoxy-2-phenyl-acetophenone, substituted alpha-ketols such as 2-methyl-2-hydroxypropiophenone, aromatic sulphonyl chlorides such as 2-naphthalene sulphonyl chloride, photoactive oximes such as 1-phenyl-1,1-propanedione-2-(O-ethoxycarbonyl)oxime. Each of the crosslinking agents is useful in the range of from about 0.01% to about 3%, preferably 0.1 to 1 percent, of the total components.

Other useful materials which can be blended into the adhesive matrix include, but are not limited to, fillers, pigments, plasticizers, tackifiers, fibrous reinforcing agents, woven and nonwoven fabrics, foaming agents, antioxidants, stabilizers, fire retardants, and rheological modifiers. Chain transfer agents, such as carbon tetrabromide, mercaptane or alcohols, can be used in the monomer mixture to adjust the molecular weight of the monomer.

The adhesive is formulated by mixing water and the monomers with optional hydrophobic polymer, surfactants, chain transfer agent, crosslinker and then heating under an inert ($O_2$ free) atmosphere while treating with initiator. The reaction latex mixture can be mixed with other optional additives and coated with the microspheres as an adhesive mixture by any conventional method.

The microsphere/adhesive matrix mixture is coated onto a backing which generally is a thin water impermeable backing, preferably a thermoplastic film, which is most preferably a thin polyethylene polymer, copolymer or blend. The microsphere/adhesive matrix is generally in a ratio of about 1–60 parts microspheres to 99–40 parts adhesive matrix based on 100 parts of the adhesive mixture, preferably 1 to 40 parts microsphere and most preferably 1 to 20 parts of the microspheres.

The water impermeable backing layer can be treated, such as by corona discharge, to improve adhesion by the microsphere/adhesive matrix. Further layers can be provided depending on the end use of the repositionable and linerless adhesive/backing laminate. Absorbent layers and liquid permeable cover layers are used for sanitary napkins or adult incontinent pads where the repositionable linerless adhesive would be used to attach to the wearer's undergarment keeping the absorbent product in place. With bed liners, the laminate could directly adhere to the bed fabric or cotton sheet with or without a liquid absorbent layer attached to the opposite face of the backing, generally a liquid impermeable film layer.

To provide a functional bonding to the undergarment, bed, or the like, the adhesive should have a T peel-to-fabric of at least 25 gm/25 mm, preferably at least 40 gm/25 mm to conventional fabric such as woven cotton and nylon. The microsphere content in the adhesive mixture generally is at least 1%, preferably 2%, and most preferably at least 5% to ensure that the adhesive has the desired balance of high adhesion to fabric and releasability without adhesive transfer, such that a protective release liner is not required.

The adhesion to the backing is generally greater than the adhesion to the fabric, preferably at least 1.25 times the adhesion to the fabric. Generally, the adhesion to the backing is at least 700 gm/25 mm, preferably greater than 1000 gm/25 mm to insure that the adhesive does not transfer to the fabric in use, or to adjacent articles or packaging material, or to the back side of the backing layer when in a roll form. In a preferred arrangement, the microsphere/adhesive matrix coating is applied to a thin liquid impermeable backing film on one face, and then wound into roll form without any release liner on the opposing face of the backing film. This tape laminate can then be used directly in the production of sanitary napkins and adult incontinence pads without need for direct adhesive coating on the production line and where the tape film backing can be used to form the liquid impermeable backing, or backsheet, of the sanitary napkin or adult incontinent pad. This is extremely advantageous in terms of manufacturability. The invention adhesive provides unwind values of less than 400 gm/25 mm and generally as low as 300 gm/25 mm and below without any release coating. A release coating would interfere with subsequent attachment of layers, such as the absorbent pad, to the liquid impermeable film backside.

The following tests were used to evaluate the microsphere adhesive tapes.

T-Peel Adhesion Test to Cotton and Nylon Fabric

The test was carried out at constant temperature and humidity (23° C. and 50% relative humidity) and the test fabric and adhesive tape samples were conditioned for 24 hours prior to testing. The test fabric was cut into a 2 inch×5 inch (5.1 cm×12.7 cm) piece. A 1 inch×5 inch (2.5 cm×12.7 cm) sample of the microsphere adhesive tape was placed adhesive side down onto the test fabric and the tape/fabric laminate was then rolled down using two passes of a 100 gram rubber roller. Approximately 1.5 inch (3.8 cm) of the tape was carefully peeled from the test fabric by hand. The fabric layer was then placed in the lower jaw of a constant rate "INSTRON™" tensile tester and the microsphere adhesive tape was placed in the upper jaw of the tensile tester. At a crosshead speed of 20 inches (51 cm) per minute a chart recorder set at a chart speed of 10 inches (25 cm) per minute was used to record the force required to peel the microsphere adhesive tape from the fabric in a T-peel mode (180 degrees). The reported force (grams/25 mm width) required to remove the tape from the fabric is an average of at least three tests. The cotton fabric used for testing was a knit jersey cotton (Style #437, available from Testfabrics, Inc., Middlesex, N.J.). The nylon fabric used for testing was a nylon tricot (ID# T60, available from Kieffer's Lingerie Inc., Jersey City, N.J.). These fabrics are similar to what one would find in the crotch portion of women's briefs.

Heat Aged T-Peel Adhesion Test to Cotton and Nylon Fabric

This test was carried out in the manner described above except that the tape/fabric laminates were prepared using two passes of a 100 gram rubber roller plus two passes of a 4.5 lb (2 kg) rubber roller. Prior to testing the tape/fabric laminates were aged in a 105° F. (49° C.) oven for four hours under a weight such that the pressure exerted was equivalent to 400 grams per inch$^2$ (62 gram per cm$^2$). The laminates were then allowed to cool for 15 minutes and peel testing was completed within 2 hours after the samples had been cooled. The data reported(grams/25 mm) is an average of five tests, one sample being tested each day within a five day period.

2-Bond Failure Test

This test provides a measure of how strongly an adhesive is anchored to a film backing. The test was carried out at constant temperature and humidity (23° C. and 50% relative humidity) and the microsphere (or other test tape) adhesive tape samples were conditioned for 24 hours prior to testing. A 1 inch×5 inch (2.5 cm×12.7 cm) sample of the microsphere adhesive tape was placed adhesive side up onto a piece of double-coated adhesive tape that had been securely adhered to a 2 inch×5 inch (5.1 cm×12.7 cm) steel panel. A silicone release liner was placed on top of the microsphere adhesive tape sample and the laminate was then rolled down using two passes of a 4.5 lb (2 kg) rubber roller. The liner was removed and a 0.5 inch (1.3 cm) width piece of 3M "SCOTCH™" Masking Tape (#2543303) was placed adhesive side down on top of the microsphere adhesive tape sample. The silicone release liner was placed on top of the sample again and the laminate was then rolled down using two passes of a 4.5 lb (2 kg) rubber roller. The liner was then removed. Using an "INSTRON™" tensile tester, at a crosshead speed of 12 inches (30.5 cm) per minute the masking tape was peeled from the adhesive tape sample at a 90 degree angle. Results are reported in grams/25 mm width. Reported values are an average of at least three tests.

Unwind Test

The test was carried out at constant temperature and humidity (23° C. and 50% relative humidity) and the roll of microsphere adhesive tape (or other test tape) was conditioned for 24 hours prior to testing. Three laps of the microsphere tape were removed from the roll and the microsphere tape was folded over at its free end to form a tab. The roll of microsphere tape was then placed on the spindle of an unwind apparatus and the apparatus was placed in the lower jaw of a constant rate "INSTRON™" tensile tester making sure that the spindle was able to turn freely. The tape tab was then placed in the upper jaw of the tensile tester. At a crosshead speed of 20 inches (51 cm) per minute a chart recorder set at 10 inches (25 cm) per minute was used to record the unwind value for unwinding approximately 6 inches (15 cm) of tape. The unwind values are reported in grams/25 mm width. Reported values are an average of at least three tests.

Examples 1–7, Comparative Examples 8–10

Hollow, polymeric microspheres (94:6 isooctyl acrylate-:acrylic acid), having an average diameter of approximately 90 microns were prepared in accordance with U.S. Pat. Nos. 5,045,569 and 5,053,436. A stable aqueous microsphere suspension of 25 percent solids by weight was used in example 4. For all examples except 4, the microspheres suspension was concentrated to 49 percent solids by weight of microsphere by allowing the suspension to separate into two layers. The upper layer containing a concentrated microsphere suspension and the lower layer, consisting of essentially water, were separated by removing the lower aqueous layer. The microsphere adhesive was then prepared by blending the microsphere suspension (either at 49% solids or 25% solids by weight of microspheres) with a 60% solids by weight latex pressure sensitive adhesive in amounts appropriate to providing the desired weight percent of microspheres on a dry basis (see Table I). A dilutant of 0.2 weight percent aqueous solution of an ammonium lauryl sulfate ("STANDAPOL™" A, available from Henkel AG) was used to adjust the percent solids of the microsphere and adhesive suspension to the levels reported in Table I (% solids).

The latex pressure-sensitive adhesive was prepared as described in European patent appln. no. 05 54 832 A1. The latex pressure-sensitive adhesive composition was prepared from a) 89% by weight isoctyl acrylate, b) 6% by weight vinyl acetate, c) 3% by weight acrylic acid, d) 2% by weight "PICCOLASTIC™"A-75 (a polystyrene resin available from Hercules), e) 2.5% by weight of "MAZON™" SAM-211 (an alkylene poly(alkoxyethyl) ammonium sulfate, a copolymerizable surfactant available from PPG Industries), f) 0.1% by weight of 1,6-hexanediol diacrylate crosslinking agent, g) 0.2% by weight of carbon tetrachloride chain transfer agent, and h) 0.1% by weight of potassium persulfate initiator. The weight percentages of a), b), c), and d) are each based on the total weight of those four components; the weight percentages of e), f), g), and h) are each based on the total weight of a) plus b) plus c) and d).

The microsphere/adhesive solution was then coated in a conventional fashion (% solids are given in Table I) onto the matte finished side of a 1.5 mil (37.5 microns) cast low density polyethylene ("TENITE™" 1550, available from Eastman Chemical Co.) film backing having a matte surface (Ra=44) on one side and a smooth surface on the opposite side. The side of the film having the matte surface had also been corona treated to promote the adhesion of the microsphere adhesive to the film. The coated microsphere adhesive tape was then allowed to dry for approximately 20 minutes at 150° F. (65° C.). The final adhesive thickness was approximately 6 grains/24 inch$^2$ (2.5 mgs/cm$^2$). The microsphere adhesive tape samples were tested for T-peel adhesion to the cotton and nylon fabrics. The microsphere adhesive tape samples were also tested for 2-Bond failure. Results are given in Table I.

Example 11

Example 11 (see Table I) was prepared and tested as described above except that it had no microspheres added to the acrylate latex PSA (100% latex adhesive).

TABLE I

| Example | % Microspheres | % Solids | T-Peel (Cotton) | T-Peel (Nylon) | #2-Bond |
|---|---|---|---|---|---|
| 1 | 2 | 50 | 71 | 110 | 1841 |
| 2 | 9 | 34 | 66 | 55 | 1300 |
| 3 | 10 | 46 | 69 | — | * |
| 4 | 16 | 49 | 79 | 84 | * |
| 5 | 22 | 57 | 43 | 71 | 1549 |
| 6 | 35 | 56 | 49 | 59 | 1639 |
| 7 | 55 | 53 | 29 | 40 | 926 |
| C8 | 70 | 52 | 11 | 24 | 1235 |
| C9 | 82 | 51 | 9 | 11 | 935 |
| C10 | 98 | 49 | 6 | 10 | 1282 |
| 11 | 0 | 60 | 103 | 102 | * |

*bond strength was greater than the tensile strength of the film backing

These examples show that below approximately 60% by weight of hollow microspheres in an acrylate latex adhesive a balance of good adhesion to cotton and nylon fabrics and strong anchorage to the backing is achieved. The T-peel adhesions to cotton and nylon begin to decrease unacceptably above approximately 60% by weight of hollow microspheres in the adhesive. The 2-Bond failure data was acceptable for all the above examples demonstrating good anchorage of the adhesives to the polyethylene film backing.

The latex PSA with no microspheres has the balance of properties that are desirable for use as an attachment adhesive for feminine hygiene pads but would not have the feature of being repositionable and being able to be packaged without a protective release liner due to the high level of adhesion.

Examples 12–17

Examples 12–17 were prepared in a manner identical to that described above except that smaller average diameter microspheres were utilized. These samples were also tested for T-peel adhesion to cotton and nylon fabrics and for 2-Bond failure (see Table II).

TABLE II

| Example | Microsphere diameter | % Microspheres | % Solids | T-Peel (Cotton) | T-Peel (Nylon) | #2-Bond |
|---|---|---|---|---|---|---|
| 12 | 40 | 15 | 35 | 63 | 84 | 1558 |
| 13 | 40 | 19 | 38 | 52 | 57 | 1435 |
| 14 | 40 | 29 | 42 | 71 | 69 | 1407 |
| 15 | 19 | 15 | 35 | 45 | 48 | 1614 |
| 16 | 19 | 19 | 38 | 66 | 84 | 1725 |
| 17 | 19 | 29 | 42 | 86 | 72 | 1938 |

These examples show that microsphere adhesive tapes prepared from microspheres having average diameters of less than 90 microns also exhibit a good balance of adhesion properties to cotton and nylon fabrics and strong anchorage to the polyethylene film backing.

Example 18

Microsphere adhesive tape samples identical to Example 3 above were prepared. Samples were tested for T-peel adhesion to cotton and nylon fabrics. Two passes of a 4.5 lb (2 kg) rubber roller were used for the rolldown instead of a 100 gram rubber roller in preparing the other samples for testing. The T-peel values were 178 and 148 grams/25 mm width, respectively. The samples were then heat aged and were tested again for T-peel adhesion. The average value for T-peel adhesion to cotton after heat aging was 302 grams/25 mm width. The average value for T-peel adhesion to nylon after heat aging was 268 grams/25 mm width. There was no transfer of the adhesive to the fabrics after heat aging.

This example demonstrates that the T-peel adhesion from cotton and nylon increases after heat aging but is still acceptable.

Example 19

A roll of microsphere adhesive tape was prepared having the same microsphere adhesive composition as Example 3 above by coating approximately 40 yards (37 m) of a 6 inch (15 cm) wide roll of the polyethylene film backing with the microsphere adhesive by means of a knife coater. Again the microsphere adhesive was coated onto the side of the polyethylene film that had a matte surface and had also been corona treated to promote the adhesion of the microsphere adhesive to the film. The microsphere adhesive tape was then wound upon itself (without a primer coating to increase adhesive anchorage, or a release liner or low adhesion backsize coating, LAB) into roll form onto a 3.25 inch (8.3 cm) diameter core. The roll of microsphere/adhesive matrix tape was then slit into 1 inch (2.5 cm) width rolls. The rolls were heat aged for 6 months at 120° F. (49° C.). Unwind values were measured before and after heat aging. Tape samples were also removed from the rolls after heat aging and were tested for T-peel adhesion to cotton and for 2-Bond failure. Test results are given in Table III.

TABLE III

| Test Values for Example 19 | |
|---|---|
| Unwind (initial) | 285 |
| Unwind (heat aged) | 260 |
| T-Peel (cotton) | 47 |
| 2-Bond | 1725 |

This example demonstrates that a roll of microsphere adhesive tape can be prepared without a primer coating, or a release liner or a LAB coating on the side of the tape opposite the adhesive and still have acceptable unwind values even after extensive heat aging. This example also demonstrates that the peel performance from cotton remains acceptable for the tape even after an extended period of heat aging. In addition, no adhesive transfer to the side of the tape opposite the adhesive was observed.

Examples 20 and Comparative Examples 21–23

Microsphere adhesive tape samples identical to Example 3 above were prepared and were tested for T-peel adhesion to cotton and nylon fabrics. The samples were tested as described above except that when the tape/fabric sample were prepared they were rolled down two times with a 4.5 lb (2 kg) rubber roller instead of a 100 gram rubber roller. Adhesive attachment systems from three commercially available feminine hygiene pads were also tested for comparison. Results are summarized in Table IV.

TABLE IV

| Example | Sample type | T-Peel (Cotton) | T-Peel (Nylon) |
|---|---|---|---|
| 20 | microsphere adhesive | 232 | 293 |
| C21 | "STAYFREE ™" (maxi) | 178 | 110 |
| C22 | "SURE & NATURAL ™" (maxi) | 272 | 200 |
| C23 | "SURE & NATURAL ™" (panty liner) | 239 | 180 |

These examples demonstrate that the linerless microsphere/adhesive tape performs comparably to commercially available linered adhesive attachment systems for sanitary napkins.

Examples 24–27

Several different acrylate based PSA tapes were tested for T-peel adhesion to cotton (with a 4.5 lb rolldown) and for 2-Bond failure in an effort to identify other acrylate adhesives that might have the balance of properties of good adhesion to cotton and a strong bond to the polyethylene backing which would be desirable for the microsphere/adhesive tape. The tape samples were prepared with no microspheres. An example similar to Example 11 above was also included as a control. Results are given in Table V. All samples were coated to the same thickness as Example 11 above.

TABLE V

| Example | Adhesive Type | T-Peel (cotton) | 2-Bond |
|---|---|---|---|
| 24 | A | 115 | 1300 |
| 25 | B | 238 | 1492 |
| 26 | C | 88 | 1450 |
| 27 | D | 347 | 2347 |

A = Pressure-sensitive adhesive used in 3M Micropore ™ First Aid Tape #1530
B = Pressure-sensitive adhesive used in 3M Scotch ™ Magic ™ Tape #810
C = Pressure-sensitive adhesive used in 3M Outdoor Window Film Mounting Tape #2175
D = Control (similar to Example 11)

These examples show that other acrylate based adhesives have a balance of properties of good peel adhesion to cotton and strong anchorage to the polyethylene film which could make them desirable to utilize in microsphere adhesive compositions. However, these adhesives are not as good as control adhesive D and the microsphere level would preferably be less than 50 parts for 100 parts of microsphere/adhesive mixture.

Examples 28–36

Microsphere adhesive samples were prepared from the acrylate pressure-sensitive adhesives used in Examples 24–26. The same microspheres (90 microns in diameter) that were used in Examples 1–10 were blended with the adhesives and tape samples were prepared in a manner similar to that described for the previous examples ("TENITE™" 1550 polyethylene film backing, 2.5 mgs/cm² adhesive coating thickness). The microsphere/adhesive tapes were then tested for T-peel adhesion to cotton and nylon fabrics, and for 2-Bond failure. Results are summarized in Table VI.

TABLE VI

| Example | % Microspheres | Adhesive Type | T-Peel (Cotton) | T-Peel (Nylon) | #2-Bond[1] |
|---|---|---|---|---|---|
| 28 | 10 | A | 30 | 48 | >2350 |
| 29 | 21 | A | 19 | 40 | >2200 |
| 30 | 36 | A | 23 | 39 | >1900 |
| 31 | 10 | B | 22 | 41 | >1600 |
| 32 | 20 | B | 22 | 21 | >1200 |
| 33 | 37 | B | 28 | 31 | >1400 |
| 34 | 11 | C | 15 | 38 | >1200 |
| 35 | 21 | C | 12 | 22 | >1200 |
| 36 | 38 | C | 19 | 21 | >1300 |

[1] the 2-Bond values were all so high that an estimate of the force was taken before the deformation of the film backing occurred These examples demonstrate that other acrylate based pressure-sensitive adhesives can be used to make functional microsphere/adhesive tapes. The peel values obtained for Examples 34–36 were lower than those obtained for Examples 28–33, as expected, based on the data obtained for Example 26 above.

Example 37 and Comparative Examples

Seven prototype sanitary napkins were prepared using the microsphere/adhesive tape as an attachment means by adhering pieces of microsphere/adhesive tape, like that described for Example 3, to the bottom of adhesive-free panty liners. The microsphere/adhesive tapes were attached to the pads through the use of a double-coated adhesive tape. The panty liners were then stacked one on top of each other so that the microsphere adhesive was in contact with the nonwoven topsheet of the panty liner below it. The stack of panty liners was then heat aged at 120° F. (49° C.) for 3 months. The panty liners were tested for T-peel adhesion to cotton before and after heat aging. Initial T-peel values averaged 36 grams/25 mm width. T-peel values after heat aging averaged 48 grams/25 mm width. There was no transfer of the microsphere adhesive to the nonwoven topsheet that it had been in contact with, nor was there any distortion or tearing of the topsheet.

Sanitary napkins were also prepared that utilized 100% latex pressure-sensitive adhesive tape (no microspheres) as the attachment means. The adhesive attachment systems of seven commercially available panty shields ("CAREFREE™", available from the Personal Products Division of McNeil-PPC, Inc.) and seven commercially available maxi pads ("ALWAYS" Ultra Plus Slender Maxi Pads with wings, Available form Procter & Gamble Co.) were replaced with pieces of adhesive tape like that described for Example 11. The panty shields were then stacked one on top of each other as described above and were heat aged at 120° F. (49° C.) for 15 days. On separating the pads it was observed that either the adhesive had transferred to the topsheet that it had been in contact with, or in the case of the "CAREFREE™" panty shields, the adhesive tore the nonwoven topsheet and so many nonwoven fibers had adhered to the adhesive that it was no longer functional.

To compare commercially available attachment adhesives, the protective release liners were removed from three "CAREFREE™" panty shields and the panty shields were stacked one on top of each other. Immediately on separating the panty shields from each other (no heat aging) the attachment adhesive tore the nonwoven topsheet that it had been in contact with. The protective release liners were also removed from three "ALWAYS™" Ultra Plus Slender Maxi Pads and the pads were stacked one on top of each other. The pads were immediately separated from each other and transfer of the attachment adhesive to the "DRI-WEAVE™" topsheet was observed.

These examples demonstrate the repositionability of the microsphere/adhesive tapes by showing that pads using the microsphere adhesive mixture can be stacked one on top of the other without the use of a protective release liner. The microsphere adhesive tape still exhibited good adhesion to cotton after being in contact with the nonwoven topsheet over a prolonged period of time at an elevated temperature and there was no transfer of the microsphere adhesive to the topsheet.

Example 38

Microsphere/adhesive tapes like that described for Example 3 were prepared. Three pieces of tape were then taken and adhered to the inside portion of films that are typically used to package individual feminine hygiene pads or sanitary napkins. The films used were obtained from the individual packages provided with commercially available "MAXITHINS™" panty liners (available from Hospital Specialties). The microsphere adhesive tape/packaging film laminates were heat aged at 120° F. (49° C.) for 6 months. After this time the microsphere adhesive tapes were peeled off of the packaging film. No transfer of the adhesive to the packaging film was observed.

This example demonstrates that feminine hygiene pads having the microsphere adhesive as the attachment means could be individually packaged without having a protective release liner on the microsphere adhesive.

The various modifications and alterations of this invention will be apparent to those skilled in the art without departing from the scope and spirit of this invention, and this invention should not be restricted to that set forth herein for illustrative purposes.

We claim:

1. A disposable absorbent article having a linerless adhesive attachment region comprising a liquid permeable cover layer, an absorbent layer and a liquid impermeable backing layer and a linerless adhesive fastening region on at least one face of said backing layer, which adhesive comprises:
   (a) 1 to 60 parts of an elastic, tacky, solvent and water insoluble, solvent or water dispersible polymeric microspheres, comprising:
      (i) at least 70 parts of at least one free radically polymerizable monomers of any acrylate, methacrylate or vinyl ester;
      (ii) 0 to 30 parts of at least one polar monomer; and
      (iii) 0 to 30 parts of at least one hydrophilizing component; and
   (b) 99 to 40 parts of an aqueous latex, emulsion polymerized acrylate pressure-sensitive adhesive matrix providing 100 parts adhesive, the adhesive having a T-peel to cotton or nylon fabric of at least 25 gm/25 mm without significant adhesive transfer from the backing.

2. The disposable article of claim 1 wherein the microspheres have an average diameter of from 1 to 300 microns.

3. The disposable article of claim 1 wherein the microspheres have an average diameter of from 1 to 150 microns.

4. The disposable article of claim 1 wherein the microspheres have an average diameter of from 20 to 150 microns.

5. The disposable article of claim 1 wherein the microspheres comprise an acrylate polymer or copolymer having a glass transition temperature of less than about −10° C.

6. The disposable article of claim 5 wherein the microspheres comprise adhesive microspheres of:
   (a) at least 70 parts of at least one free radically polymerizable monomers of any acrylate, methacrylate or vinyl ester;
   (b) 0 to 30 parts of at least one polar monomer; and
   (c) 0 to 30 parts of at least one hydrophilizing component, and the adhesive has a T-peel to cotton or nylon fabric of at least 40 gm/25 mm.

7. The disposable article of claim 6 wherein the free radically polymerizable monomer comprises an alkyl acrylate, alkyl-methacrylate, vinyl ester or mixtures thereof, and the alkyl is a $C_4$ to $C_{12}$ alkyl.

8. The disposable article of claim 7 wherein the adhesive microspheres comprise:
   (a) 80 to 100 parts of the free radically polymerizable monomer;
   (b) 0 to 10 parts of the polar monomer; and
   (c) 0 to 10 parts hydrophilizing component.

9. The disposable article of claim 8 wherein the adhesive microspheres comprise:
   (a) 90 to 100 parts of the free radically polymerizable monomer;
   (b) 0 to 10 parts of the polar monomer; and
   (c) 0 to 10 parts hydrophilizing component.

10. The disposable article of claim 9 wherein the polar monomer is selected from the group consisting of acrylic acid, methacrylic acid, itaconic acid, crotonic acid, maleic acid, fumaric acid, sulfoethyl methacrylate, and ionic monomers such as sodium methacrylate, ammonium acrylate, sodium acrylate, trimethylamine p-vinyl benzimide, 4,4,9-trimethyl-4-azonia-7-oxo-8-oxa-dec-9-ene-1-sulphonate, N,N-dimethyl-N-(beta-methacryloxy-ethyl)ammonium propionate betaine, trimethylamine methacrylimide, 1,1-dimethyl-1-(2,3-dihydroxypropyl)amine methacrylimide, N-vinyl pyrrolidone, N-vinyl caprolactam, acrylamide, t-butyl acrylamide, dimethyl amino ethyl acrylamide, N-octyl acrylamide, mixtures thereof.

11. The disposable article of claim 10 wherein the hydrophilizing component comprises poly(alkylene oxides), poly(vinyl methyl ether), poly(acrylamide), poly(n-vinylpyrrolidone), poly(vinyl alcohol), and mixtures thereof.

12. The disposable article of claim 10 wherein the adhesive microspheres comprise 97 to 99.9 parts of the free radically polymerizable monomer, 0.1 to 1.0 parts polar monomer and 0 to 1.0 parts hydrophilizing component.

13. The disposable article of claim 7 wherein for each 100 parts adhesive in the microspheres there further comprises:
   (d) 0.01 to about 10 parts of an initiator; and
   (b) up to 0.15 percent crosslinking functional polymerizable group per total polymerizable groups.

14. The disposable article of claim 1 wherein the acrylate adhesive comprises a latex adhesive having a Tg less than 0° C. comprising:
   (a) at least about 70 percent of an alkyl acrylate monomer;
   (b) 0 to 30 percent of a polar monomer; and
   (c) 0 to 20 percent of a monomer having a Tg higher than the alkyl acrylate.

15. The disposable article of claim 14 wherein the latex adhesive alkyl acrylate comprises a $C_2$ to $C_{14}$ alkyl acrylate of a monofunctionally unsaturated acrylate ester of a nontertiary alkyl alcohol.

16. The disposable article of claim 15 wherein the latex adhesive alkyl acrylate adhesive comprises isooctyl acrylate, isononyl acrylate, 2-ethylhexyl acrylate, butyl acrylate or mixtures thereof.

17. The disposable article of claim 15 wherein the latex adhesive higher Tg monomer comprises a vinyl ester, a $C_1$ to $C_{14}$ alkyl ester of (meth)acrylic acid, styrene or mixtures thereof.

18. The disposable article of claim 15 wherein the latex adhesive polar monomer comprises monoolefinic mono- and dicarboxylic acids, hydroxyalkyl acrylates, cyanoalkyl acrylates, acrylamides or substituted acrylamides, or from moderately polar monomers such as N-vinyl pyrrolidone, acrylonitrile, vinyl chloride or diallyl phthalate.

19. The disposable article of claim 14 wherein the latex adhesive polar monomer comprises 0 to 20 percent of the adhesive.

20. The disposable article of claim 14 wherein the latex adhesive further comprises:

(d) 0 to 20 percent of a low molecular weight hydrophobic polymer.

21. The disposable article of claim 20 wherein the latex adhesive hydrophobic polymer comprises polystyrene resin, poly(methylmethacrylate) resin, polybutadiene, polyisoprene, poly(alphamethylstyrene), polydiene-polyaromatic arene copolymers, rosin esters, and mixtures thereof having an average molecular weight of from 400 to 50,000.

22. The disposable article of claim 20 wherein the latex adhesive further comprises:

(e) 1 to 10 percent of an ionic copolymerizable surfactant based on the total adhesive components ((a)–(d)).

23. The disposable article of claim 20 wherein the latex adhesive further comprises, based on the total components ((a)–(d)):

(f) 0.01 to 3 percent initiator; and (g) 0.01 to 3 percent crosslinking agent.

24. The disposable article of claim 23 wherein the backing layer comprises a thin liquid impermeable polymer film.

25. The disposable article of claim 24 wherein the polymer film backing layer comprises a polyethylene polymer, copolymer or blend film, and the adhesive has a 2 bond adhesion of at least 700 gm/25 mm to the backing layer.

26. The disposable article of claim 1 wherein the disposable article comprises a sanitary napkin.

27. The disposable article of claim 1 wherein the disposable article comprises an incontinent pad.

28. The disposable article of claim 1 wherein the adhesive comprises 1 to 40 parts microspheres.

29. The disposable article of claim 1 wherein the adhesive comprises 1 to 20 parts microspheres.

30. The disposable article of claim 1 wherein the adhesive comprises greater than 2 percent microspheres.

31. The disposable article of claim 1 wherein the adhesive comprises greater than 5 percent microspheres.

\* \* \* \* \*